(12) United States Patent
Lensing et al.

(10) Patent No.: US 7,282,374 B1
(45) Date of Patent: Oct. 16, 2007

(54) METHOD AND APPARATUS FOR COMPARING DEVICE AND NON-DEVICE STRUCTURES

(75) Inventors: Kevin R. Lensing, Austin, TX (US); Matthew S. Ryskoski, Kyle, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 423 days.

(21) Appl. No.: 10/980,517

(22) Filed: Nov. 3, 2004

(51) Int. Cl.
*H01L 21/00* (2006.01)

(52) U.S. Cl. ............. 438/5; 438/6; 438/7; 438/10; 438/11; 438/14; 438/16; 438/17; 438/18; 257/E21.525; 356/4.01; 356/5.09

(58) Field of Classification Search ............ 438/5, 438/6, 7, 10, 11, 14, 16, 17, 18; 257/E21.525; 356/4.01, 5.09
See application file for complete search history.

(56) References Cited

U.S. PATENT DOCUMENTS

| | | | |
|---|---|---|---|
| 6,556,947 B1* | 4/2003 | Scheiner et al. | 702/172 |
| 6,582,863 B1* | 6/2003 | Stirton et al. | 430/30 |
| 6,587,744 B1* | 7/2003 | Stoddard et al. | 700/121 |
| 6,697,153 B1* | 2/2004 | Wright et al. | 356/237.4 |
| 6,751,343 B1* | 6/2004 | Ferrell et al. | 382/145 |
| 6,972,576 B1* | 12/2005 | Lyons et al. | 324/699 |
| 7,171,536 B2* | 1/2007 | Chang et al. | 711/170 |
| 2004/0080998 A1* | 4/2004 | Chang et al. | 365/200 |

OTHER PUBLICATIONS

Wolf et al., Silicon Processing for the VLSI Era, 1986, Lattice Press, vol. 1, p. 235.*

* cited by examiner

*Primary Examiner*—Matthew Smith
*Assistant Examiner*—Thanh Van Pham
(74) *Attorney, Agent, or Firm*—Williams, Morgan & Amerson, P.C.

(57) ABSTRACT

The present invention provides a method and apparatus for comparing device and non-device structures. The method includes determining at least one characteristic parameter associated with at least one non-device structure on at least one workpiece and determining at least one characteristic parameter associated with at least one device structure on the at least one workpiece. The method also includes comparing the at least one characteristic parameter associated with the at least one non-device structure and the at least one characteristic parameter associated with at least one device structure.

23 Claims, 5 Drawing Sheets

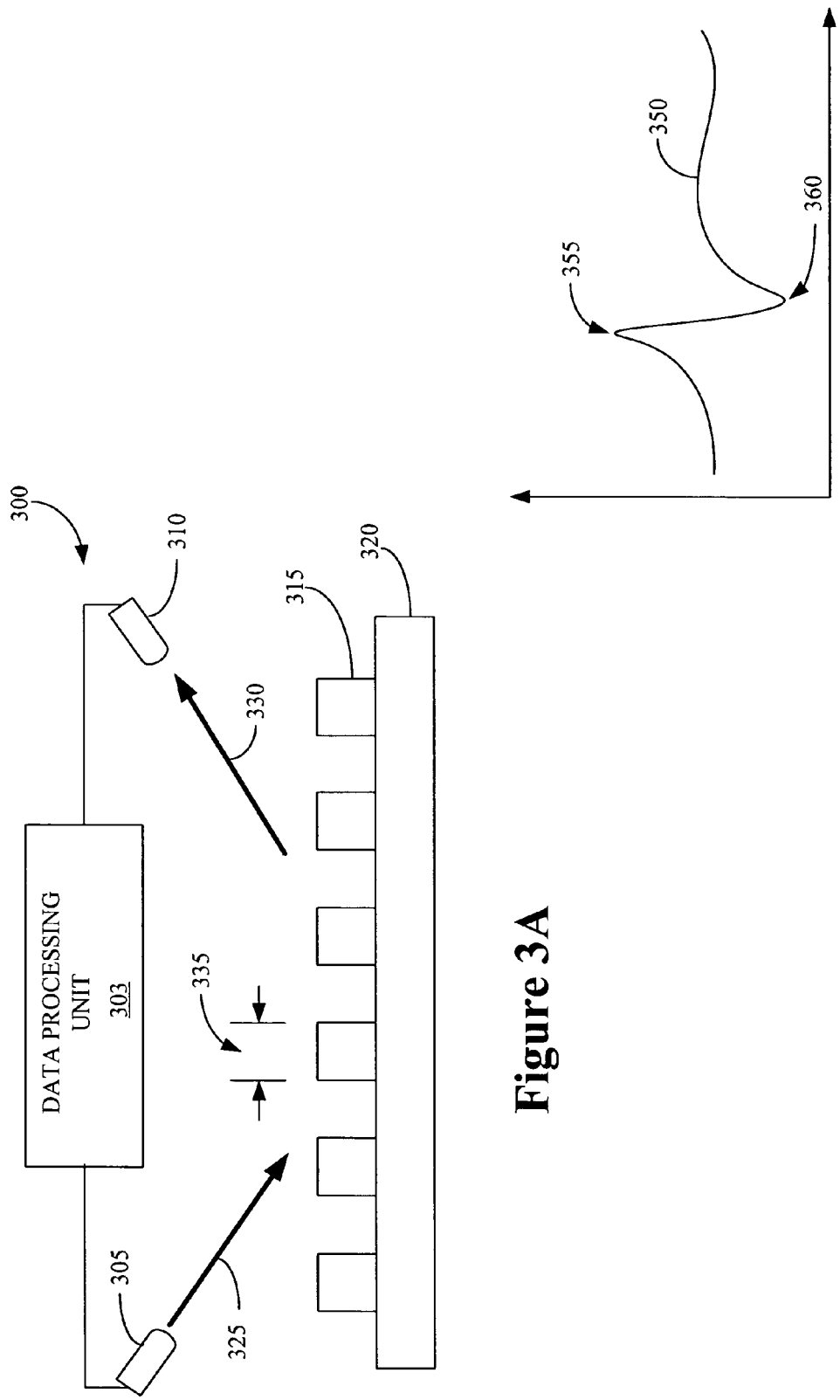

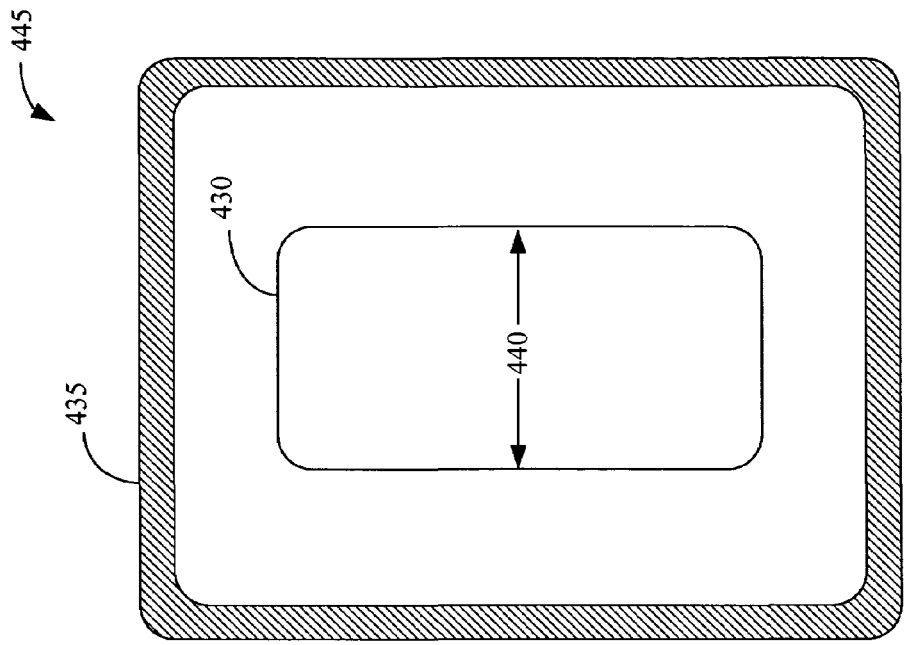
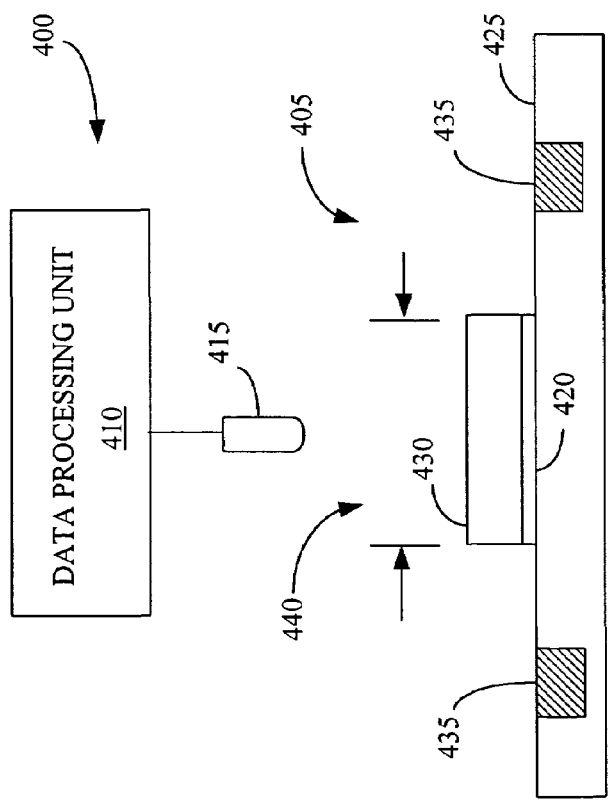
Figure 4B
Figure 4A

METHOD AND APPARATUS FOR COMPARING DEVICE AND NON-DEVICE STRUCTURES

BACKGROUND OF THE INVENTION

1. Field of the Invention

This invention relates generally to the field of semiconductor device manufacturing and, more particularly, to a method and apparatus for comparing device and non-device structures.

2. Description of the Related Art

To fabricate a semiconductor device, a wafer is typically processed in numerous processing tools in a predetermined sequence. The processing tools may include photolithography steppers, etch tools, deposition tools, polishing tools, rapid thermal processing tools, implantation tools, and the like. Each processing tool modifies the wafer according to a particular operating recipe. For example, a photolithography stepper may be used to form a patterned layer of photoresist above the wafer. Features in the patterned layer of photoresist correspond to a plurality of features, e.g. gate electrode structures, which will ultimately be formed above the surface of the wafer. The features formed on the wafer must meet appropriate design and performance criteria. Thus, various types of metrology tools may be used to measure characteristic parameters associated with the features formed on the wafer, such as critical dimensions of the features.

Integrated metrology tools, i.e. metrology tools that are coupled to a processing tool, may be used to measure characteristic parameters associated with the features formed on the wafer by the processing tool. Integrated metrology tools typically have a high throughput, which may enable the integrated metrology tool to measure characteristic parameters associated with substantially all the wafers in a batch. However, the high throughput of such integrated metrology tools often comes at a cost. At least in part to maintain the desired throughput, the integrated metrology tools typically perform these measurements on predetermined, non-device structures formed on the wafer. For example, a scatterometry tool may be capable of measuring a characteristic critical dimension associated with substantially every wafer in a batch, but the critical dimensions are determined using light scattered from non-device structures such as a test grating structure formed on the wafer. Thus, the characteristic parameters determined by such integrated metrology tools may not be a direct measure of the critical dimensions of devices formed on the wafer.

Stand-alone metrology tools, i.e. metrology tools that are physically separate from the processing tools, may also be used to measure characteristic parameters associated with features on a wafer. Compared to integrated metrology tools, stand-alone metrology tools typically perform higher accuracy and/or higher granularity measurements of features, including device structures, formed on the wafer. For example, a critical dimension, scanning electron microscope (CD-SEM) may be able to directly determine critical dimensions of one or more device structures formed on the wafer by analyzing an image of the structures. However, determining the critical dimensions using a CD-SEM in a stand-alone metrology tool is a more complex operation than determining a critical dimension using a scatterometer in an integrated metrology tool. Thus, stand-alone metrology tools generally have a lower throughput than the corresponding integrated metrology tools. Consequently, stand-alone metrology tools may only measure characteristic parameters associated with a subset of the wafers in a batch, which may cause the stand-alone metrology tool to miss some faults in wafers that are not monitored by the stand-alone metrology tool.

The present invention is directed to addressing the effects of one or more of the problems set forth above.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

In one embodiment of the present invention, a method is provided for comparing device and non-device structures. The method includes determining at least one characteristic parameter associated with at least one non-device structure on at least one workpiece and determining at least one characteristic parameter associated with at least one device structure on the at least one workpiece. The method also includes comparing the at least one characteristic parameter associated with the at least one non-device structure and the at least one characteristic parameter associated with at least one device structure. In other embodiments, apparatuses are provided for comparing device and non-device structures.

BRIEF DESCRIPTION OF THE DRAWINGS

The invention may be understood by reference to the following description taken in conjunction with the accompanying drawings, in which like reference numerals identify like elements, and in which:

FIG. 3A conceptually illustrates a metrology tool, in accordance with the present invention;

FIG. 3B conceptually illustrates one exemplary embodiment of metrology data that may be collected by the metrology tool shown in FIG. 3A, in accordance with the present invention;

FIG. 4A conceptually illustrates one exemplary embodiment of a CD-SEM tool, in accordance with the present invention;

FIG. 4B conceptually illustrates one exemplary embodiment of a CD-SEM image that may be formed by the CD-SEM tool shown in FIG. 4A, in accordance with the present invention.

Figure 1:
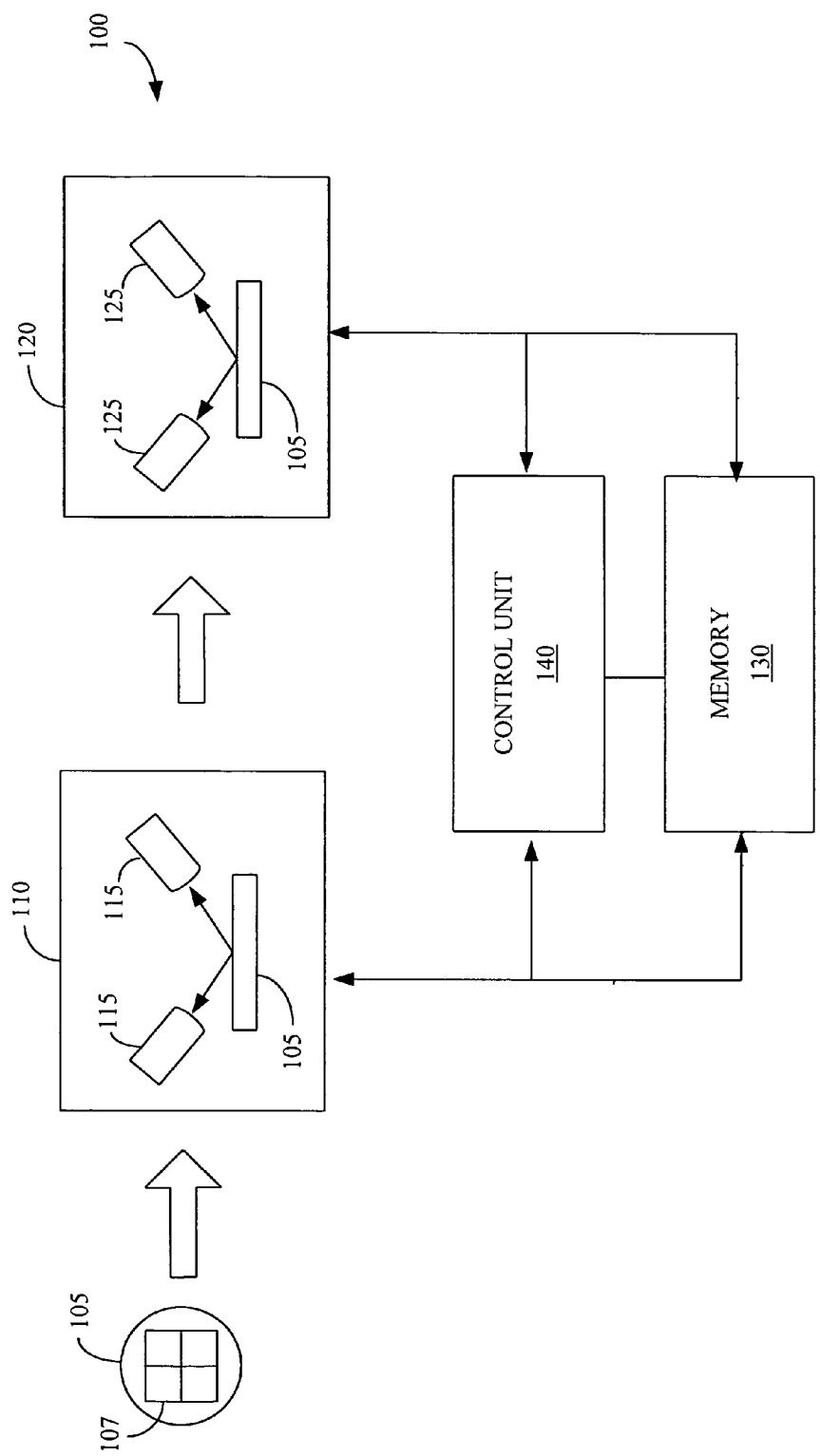
FIG. 1 conceptually illustrates a portion of a semiconductor manufacturing system, in accordance with one embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions should be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Portions of the present invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the invention are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The invention is not limited by these aspects of any given implementation.

The present invention will now be described with reference to the attached figures. Various structures, systems and devices are schematically depicted in the drawings for purposes of explanation only and so as to not obscure the present invention with details that are well known to those skilled in the art. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

FIG. 1 conceptually illustrates a portion of a semiconductor manufacturing system 100. One or more workpieces 105 may be processed by various tools within the manufacturing system 100 to form one or more semiconductor devices 107 on the workpiece 105. Persons of ordinary skill in the art should appreciate that the manufacturing system 100 typically includes numerous processing tools, such as photolithography steppers, etch tools, deposition tools, polishing tools, rapid thermal processing tools, implantation tools, and the like, which may be used to form the one or more semiconductor devices on the one or more workpieces 105. However, in the interest of clarity, the various processing tools are not shown in FIG. 1.

As will be discussed in detail below, "device" and/or "non-device" structures may be formed or may exist on the workpiece 105. As used herein, the term "non-device" refers to structures that may be formed or may exist on the workpiece 105, but that are not a functional part of any circuits, connections, and/or devices that may be formed on the workpiece 105. Non-device structures may be formed in regions of the workpiece 105 not normally used for forming devices, e.g. in the periphery region where identification codes are typically scribed or in the scribe lines between production die. As used herein, the term "device" refers to structures on the workpiece 105 that are a functional part of the circuits, connections, and/or devices that may be formed on the workpiece 105. Examples of device structures include, but are not limited to, gate structures, memory elements, lines, vias, and contacts.

The manufacturing system 100 includes at least one metrology tool 110. In one embodiment, the metrology tool 110 is an integrated metrology tool 110 that is physically coupled to a processing tool. However, in alternative embodiments, the metrology tool 110 may not necessarily be physically coupled to a processing tool or the metrology tool 110 may be coupled to a plurality of processing tools. As will be discussed in detail below, the metrology tool 110 includes one or more wafer measurement devices 115 for collecting wafer state data associated with one or more non-device structures on the workpiece 105. For example, the wafer measurement device 115 may determine one or more critical dimensions of one or more test grating structures or grids formed outside of a device region, e.g. a die, of the workpiece 105. The wafer measurement devices 115 may include scatterometers, ellipsometers, reflectometry tools, and the like. The present invention is not limited to any particular number of wafer measurement devices 115. In alternative embodiments, the metrology tool 110 may include more or fewer wafer measurement devices 115 than are shown in FIG. 1.

The manufacturing system 100 also includes at least one metrology tool 120. In one embodiment, the metrology tool 120 is a stand-alone metrology tool 120 that is not physically coupled to a processing tool. However, in alternative embodiments, the metrology tool 110 may be any desirable type of metrology tool. As will be discussed in detail below, the metrology tool 120 includes one or more wafer measurement devices 125 for collecting wafer state data associated with one or more device structures on the workpiece 105. For example, the wafer measurement devices 125 may include scanning electron microscopes, such as a critical dimension, scanning electron microscope (CD-SEM), which may determine one or more critical dimensions associated with a transistor formed on the workpiece 105. The present invention is not limited to any particular number of wafer measurement devices 125. In alternative embodiments, the metrology tool 120 may include more or fewer wafer measurement devices 125 than are shown in FIG. 1.

In operation, the workpiece 105 may be provided to the metrology tools 110, 120 in any desirable order. For example, the workpiece 105 may be provided to the metrology tool 110 so that the characteristic parameter associated with a non-device structure may be determined and then the workpiece 105 may be provided to the metrology tool 120 so that a characteristic parameter associated with a device structure may be determined. Although not shown in FIG. 1, the workpiece 105 may also be provided to any desirable processing tools before being provided to the metrology tools 110, 120, after being provided to the metrology tools 110, 120, or in between being provided to a first and a second one of the metrology tools 110, 120. Furthermore, in alternative embodiments, additional metrology tools 110, 120 may be included in the manufacturing system 100.

In one embodiment, the manufacturing system 100 includes a memory 130 for storing information related to one or more of the characteristic parameters of the device and/or non-device structures that may be formed on the wafer 105. For example, the memory 130 may be communicatively coupled to the metrology tools 110, 120 and may be used to store information indicative of the characteristic parameters of the device and/or non-device structures that are measured by the metrology tools 110, 120. As will be discussed in detail below, the memory 130 may also be used to store information indicative of one or more biases between the characteristic parameters of the device and/or non-device structures. For example, the memory 130 may be used to store historical wafer state data that may be used to determine historical biases between the characteristic parameters of device and/or non-device structures previously formed on workpieces.

A control unit 140 is communicatively coupled to the metrology tools 110, 120. In embodiments that include the memory 130, the control unit 140 is also communicatively coupled to the memory 130. In various alternative embodiments, the control unit 140 may be implemented in any desirable combination of hardware and/or software. The control unit 140 may also be part of an overall computer system that controls operations in the factory including the manufacturing system 100, such as an Advanced Process Control system. The control unit 140 is configured to compare characteristic parameters associated with non-device structures on the workpiece 105 to characteristic parameters associated device structures formed on the workpiece 105. In one embodiment, the control unit 140 is also configured to interrupt, modify, or stop operation of the manufacturing system 100 based on the comparison of the characteristic parameters associated with the device and non-device structures.

Figure 2:
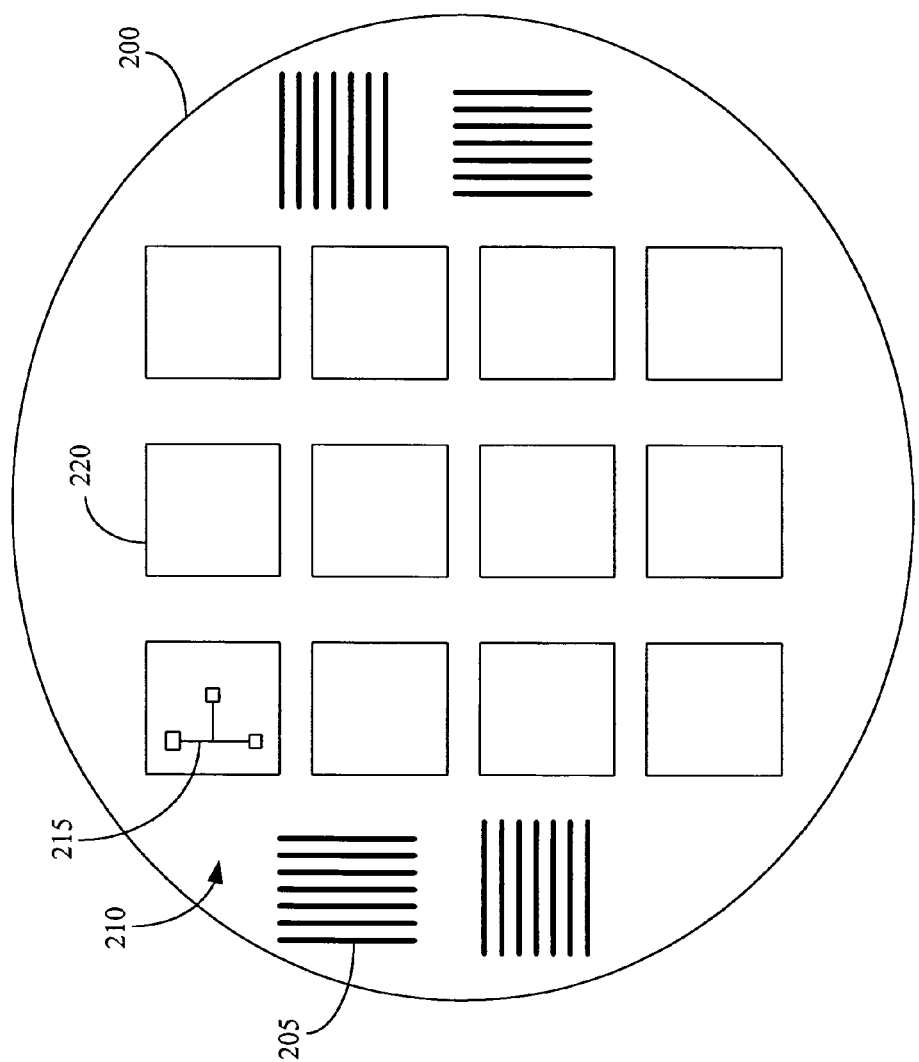
FIG. 2 conceptually illustrates one exemplary embodiment of a workpiece, in accordance with the present invention.

FIG. 2 conceptually illustrates one exemplary embodiment of a portion of a workpiece 200. In the illustrated embodiment, the workpiece 200 includes a plurality of non-device structures 205 (only one indicated). Non-device structures 205 may be formed in regions 210 of the workpiece 200 not normally used for forming devices, e.g. in the periphery region where identification codes are typically scribed or in the scribe lines between production die. In one embodiment, the non-device structures 205 include one or more periodic patterns formed on the workpiece 200, such as the non-device structures 205 used for scatterometry, ellipsometry, or reflectometry measurements. For example, the non-device structures 205 may include a repeating grating pattern including a plurality of lines, intersecting lines defining a grid, multiple gratings and/or grids formed in overlapping layers formed on the workpiece 200, and the like.

The non-device structures 205 may be formed in a variety of ways known to those of ordinary skill in the art. For example, the non-device structures 205 may include regions having a variable refractive index, trenches that may be filled with a fill material like silicon dioxide, openings between intersecting lines in a grid, an alternating pattern of doped and un-doped material, a latent photoresist pattern (i.e., the exposed and non-exposed portion have different optical characteristics and thus refract light differently), and the like. Persons of ordinary skill in the art should appreciate that any desirable number and/or type of non-device structures 205 may be formed in any desirable number and/or type of non-device regions 210 of the workpiece 200.

The illustrated embodiment of the workpiece 200 also includes a plurality of device structures 215 (only one indicated) formed in a plurality of device regions or die 220 (only one indicated). Persons of ordinary skill in the art should appreciate that any desirable number and/or type of device structures 215 and/or device regions 220 may be formed on the workpiece 200. The device structures 215 may be formed in any desirable manner.

FIG. 3A conceptually illustrates one exemplary embodiment of a metrology tool 300 for measuring characteristic parameters of non-device structures. In the illustrated embodiment, the metrology tool 300 is a scatterometer. However, the present invention is not limited to scatterometers. In alternative embodiments, the metrology tool 300 may be an ellipsometer, a reflectometer, and the like. The metrology tool 300 includes a data processing unit 303, a light source 305, and a light detector 310. The light source 305 illuminates at least a portion of a non-device structure 315 formed above a layer 320. The illuminating light (indicated by arrow 325) may be monochromatic light, white light, or some other wavelength or combinations of wavelengths, depending on the specific implementation. The angle of incidence and/or the phase of the illuminating light 325 may also vary, depending on the specific implementation.

The detector 310 takes optical measurements, such as intensity and/or phase, of light that is reflected from the non-device structure 315 and/or the layer 320 (as indicated by the arrow 330). The light analyzed by the scatterometry tool 300 typically includes a reflected component (i.e., incident angle equals reflected angle) and a refracted component (i.e., incident angle does not equal the reflected angle). For purposes of discussion here, the term "reflected" light is meant to encompass both components.

FIG. 3B conceptually illustrates one exemplary embodiment of metrology data 350 that may be collected by the metrology tool 300 shown in FIG. 3A. In the illustrated embodiment, the metrology data 350 represents the intensity of the reflected light 330 as a function of wavelength.

However, the present invention is not limited to metrology data 350 that includes a light intensity as a function of wavelength. In alternative embodiments, the metrology data 350 may include a phase of the reflected light 330 and the metrology data 350 may be represented as a function of any desirable variable including time, frequency, and the like.

The metrology data 350 may include information indicative of one or more characteristic parameters associated with the non-device structures 315. In the illustrated embodiment, the metrology data 350 includes an intensity peak 355 and an intensity trough 360, which may be indicative of one or more critical dimensions 335 of the non-device structures 315. For example, the intensity peak 325 may be indicative of a wavelength of the reflected light 330 that exhibits an increased intensity because of constructive interference of the incident light 325 that is associated with a periodicity of the non-device structures 315 on a length scale corresponding to the critical dimension 335. For another example, the intensity trough 350 may be indicative of a wavelength of reflected light 330 that exhibits a decreased intensity because of destructive interference of the incident light 325 that is associated with a periodicity of the non-device structures 315 on a length scale corresponding to the critical dimension 335.

In the illustrated embodiment, the data processing unit 303 receives the optical measurements from the detector 310 and processes the data to identify characteristic parameters associated with the non-device structures 315. For example, the data processing unit 303 may determine one or more critical dimensions 335 associated with the non-device structures 315 using optical measurements such as the metrology data 350. For example, the data processing unit 303 may determine one or more critical dimensions 335 of the non-device structures 315 based on the intensity peak 355 and/or the intensity trough 360. In the interest of clarity, techniques for determining the one or more critical dimension 335 of the non-device structures 315 will not be discussed further herein, as they are known in the art.

Referring back to FIG. 1, the characteristic parameters associated with non-device structures identified by the metrology tool 110 are provided to the control unit 140. In one embodiment, the characteristic parameters are provided directly to the control unit 140. However, in alternative embodiments, which may be practiced in combination with or instead of the previous embodiment, the characteristic parameters may be provided to the memory 130. The control unit 140 may then access the characteristic parameters by accessing the memory 130.

FIG. 4A conceptually illustrates one exemplary embodiment of a metrology tool 400 for measuring characteristic parameters of a device structure 405. In the illustrated embodiment, the metrology tool 400 is a critical dimension, scanning electron microscope (CD-SEM) tool. However, the present invention is not limited to CD-SEM tools. In alternative embodiments, the metrology tool 400 may be any desirable type of metrology tool. The metrology tool 400 includes a data processing unit 410 and a scanning electron microscope 415. However, persons of ordinary skill in the art should appreciate that the metrology tool 400 may include other components that, in the interest of clarity, are not shown in FIG. 4A.

In the illustrated embodiment, the device structure 405 is a transistor including a gate insulation layer 420 formed above a layer 425 and a gate electrode 430 is formed above the gate insulation layer 420. In one embodiment, the device structure 405 may be formed in a region that is electrically isolated by a trench isolation region 435. Although only the gate insulation layer 420 and the gate electrode 430 are shown, persons of ordinary skill in the art should appreciate that the device structure 405 may also include other elements such as a source region, a drain region, one or more sidewalls formed adjacent to gate insulation layer 420 and/or the gate electrode 430, and the like. Persons of ordinary skill in the art should also appreciate that the illustrated transistor is only one exemplary embodiment of the device structure 405. In alternative embodiments, the device structure 405 can be any desirable device including, but not limited to, other embodiments of transistors having more or fewer components, memory elements, vias, lines, and the like. In the illustrated embodiment, the device structure 405 has a critical dimension 440.

FIG. 4B conceptually illustrates one exemplary embodiment of an image 445 that may be formed by the metrology tool 400 shown in FIG. 4A. In the illustrated embodiment, the image 445 shows the gate electrode 430 and the trench isolation region 435. The critical dimension 440 of the device structure 405 may then be determined using the image 445. For example, the image 445 may be a digital image and the critical dimension 440 may be determined using a variety of known digital image processing techniques, which may be implemented in the data processing unit 410. In the illustrated embodiment, the critical dimension 440 is primarily determined by the horizontal extent of the gate electrode 430. However, in alternative embodiments, the critical dimension 440 can be determined using any desirable dimension of any desirable portion of the device structure 405, as should be appreciated by persons of ordinary skill in the art.

Figure 5:
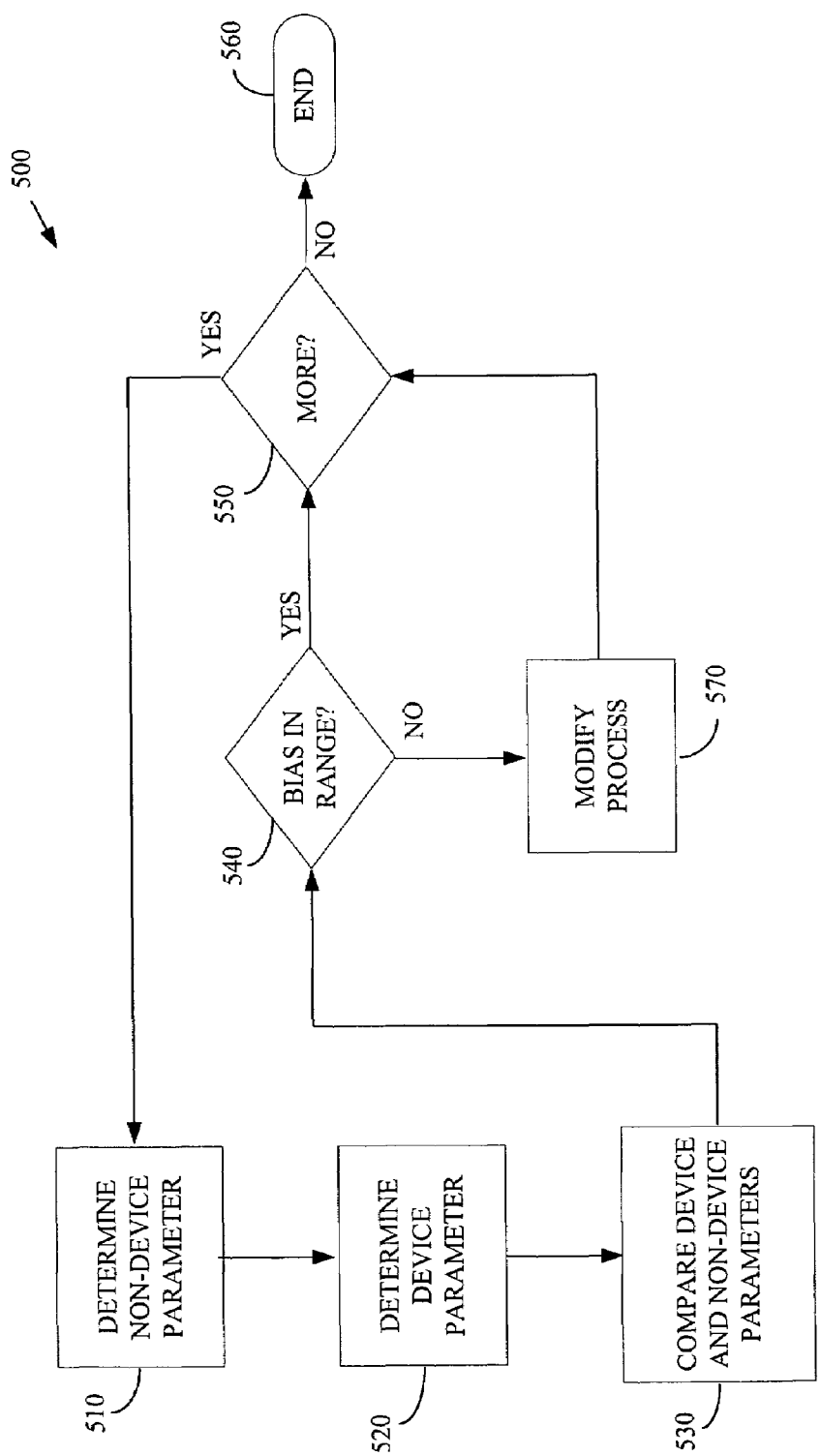
FIG. 5 conceptually illustrates one exemplary embodiment of a method of monitoring device and non-device structures, in accordance with the present invention.

FIG. 5 conceptually illustrates one exemplary embodiment of a method 500 of monitoring device and non-device structures, such as the non-device structures 205, 315 and the device structures 215, 405 shown in FIGS. 2, 3A, and 4A-B, which may be formed on a workpiece. In the illustrated embodiment, at least one characteristic parameter of at least one non-device structure is determined (at 510) and at least one characteristic parameter of at least one device structure is determined (at 520). For example, as discussed in detail above, a critical dimension associated with a non-device structure may be determined by a scatterometer and a critical dimension associated with a device structure may be determined by a CD-SEM tool. Although the previously illustrated embodiments describe determining (at 510 and/or 520) a single characteristic parameter associated with a single structure, the present invention is not limited to determining (at 510 and/or 520) a single characteristic parameter of a single structure. In one alternative embodiment, a plurality of characteristic parameters associated with one or more non-device structures may be determined (at 510). In another alternative embodiment, a plurality of characteristic parameters associated with one or more device structures may be determined (at 520).

The characteristic parameters associated with the device and non-device structures are then compared (at 530). In one embodiment, comparing (at 530) the characteristic parameters includes determining a bias between the characteristic parameters associated with the device and non-device structures. For example, a critical dimension of a non-device structure may be determined (at 510) to be approximately 100 nm and a critical dimension of a device structure may be determined (at 520) to be approximately 105 nm. In that case, the bias between the critical dimensions would be approximately 5 nm. However, the present invention is not limited to additive biases, such as described above. In one alternative embodiment, a multiplicative bias may be determined. For example, a critical dimension of a non-device structure may be determined (at 510) to be approximately 100 nm and a critical dimension of a device structure may be determined (at 520) to be approximately 500 nm. In that case, the multiplicative bias between the critical dimensions would be approximately 5.

Although the previous example describes a one-to-one comparison (at 530) of a single characteristic parameter of a single non-device structure and a single characteristic parameter of a single device structure, the present invention is not limited to one-to-one comparisons (at 530) of device and non-device structures. In various alternative embodiments, statistical combinations of characteristic parameters associated with one or more device and/or one or more non-device structures may be compared (at 530). For example, a mean value of the critical dimensions associated with a plurality of non-device structures may be compared (at 530) to a mean value of critical dimensions associated with a plurality of device structures. The bias may also be determined based on the mean values of the characteristic parameters associated with the device and none device structures. In one embodiment, the characteristic parameters of the pluralities of device and non-device structures may be correlated in any desirable manner, including auto-correlations, cross-correlations, and the like.

In one embodiment, whether or not the bias is within an allowable range is determined (at 540). The allowable range may be determined in any desirable manner. In one embodiment, the allowable range of the bias is determined using historical data indicative of historical values of the bias, the characteristic parameters of the non-device structure, the characteristic parameters of the device structure, or any other desirable information. For example, the control unit 140 shown in FIG. 1 may determine the allowable range of the bias using historical data stored in the memory 130. Alternatively, the allowable range of the bias may be determined using a model, empirical data provided to an engineer, and the like.

If it is determined (at 540) that the bias is within the allowable range, indicating that the measured values of the characteristic parameters of the device and non-device structures on the current workpiece are within an acceptable range of each other, it may be determined (at 550) whether or not additional workpieces remain to be processed. If it is determined (at 550) that additional workpieces remain to be processed, at least one characteristic parameter of at least one non-device structure on the additional workpiece is determined (at 510), at least one characteristic parameter of at least one device structure on the additional workpiece is determined (at 520), and the method 500 continues as described above. If no additional workpieces remain to be processed, the method 500 ends (at 560).

If it is determined (at 540) that the bias is not within the allowable range, indicating that the measured values of the characteristic parameters of the device and non-device structures on the current workpiece are not within the acceptable range of each other, processing of workpieces may be modified (at 570). In one embodiment, modifying (at 570) includes stopping the process. For example, a message may be sent to a workstation and/or an engineer indicating that the bias is not within the allowable range. In response to receiving the message indicating that the bias is not within the allowable range, the workstation and/or the engineer may shut down the processing flow.

In one embodiment, which may be practiced in addition to or instead of embodiments that include stopping the process in response to receiving the message indicating that the bias is not within the allowable range, modifying (at 570) includes taking a corrective action in response to receiving the message indicating that the bias is not within the allowable range. For example, one or more processing tools (not shown) may be cleaned and/or repaired in response to receiving the message indicating that the bias is not within the allowable range. Following the corrective action, the process flow may be resumed and it may be determined (at 550) whether or not additional workpieces remain to be processed. If it is determined (at 550) that additional workpieces remain to be processed, the method 500 continues as described above. If no additional workpieces remain to be processed, the method 500 ends (at 560).

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method, comprising:
   determining at least one characteristic parameter associated with at least one non-device structure on at least one workpiece;
   determining at least one characteristic parameter associated with at least one device structure on the at least one workpiece;
   comparing the at least one characteristic parameter associated with the at least one non-device structure and the at least one characteristic parameter associated with at least one device structure; and
   generating a signal indicative of results of the comparison of said at least one characteristic parameter associated with said at least one non-device structure and said at least one characteristic parameter associated with said at least one device structure to be used to trigger modification of the processing.

2. The method of claim 1, wherein determining the at least one characteristic parameter associated with the at least one non-device structure comprises determining at least one critical dimension associated with the at least one non-device structure.

3. The method of claim 2, wherein determining the at least one critical dimension associated with the at least one non-device structure comprises determining at least one critical dimension associated with at least one of a repeating grating pattern comprising a plurality of lines, a grid comprising a plurality of intersecting lines, multiple gratings formed in overlapping layers, grids formed in overlapping layers, a plurality of regions having a variable refractive index, a plurality of trenches filled with a fill material, a plurality of openings between intersecting lines in a grid, an alternating pattern of doped and un-doped material, and a latent photoresist pattern.

4. The method of claim 1, wherein determining the at least one critical dimension associated with the at least one non-device structure comprises determining the at least one critical dimension associated with the at least one non-device structure using at least one of a scatterometer, an ellipsometer, and a reflectometer.

5. The method of claim 1, wherein determining the at least one critical dimension associated with the at least one non-device structure comprises determining a plurality of critical dimensions associated with the at least one non-device structure.

6. The method of claim 5, wherein determining the at least one critical dimension comprises forming a statistical combination of the plurality of critical dimensions.

7. The method of claim 1, wherein determining the at least one characteristic parameter associated with the at least one device structure comprises determining at least one critical dimension associated with the at least one device structure.

8. The method of claim 7, wherein determining the at least one critical dimension associated with the at least one device structure comprises determining at least one critical dimension associated with at least one of a gate, a line, a via, and a deposition region formed on the wafer.

9. The method of claim 1, wherein determining the at least one critical dimension associated with the at least one device structure comprises determining the at least one critical dimension associated with the at least one device structure using a CD-SEM tool.

10. The method of claim 1, wherein determining the at least one critical dimension associated with the at least one device structure comprises determining a plurality of critical dimensions associated with the at least one device structure.

11. The method of claim 10, wherein determining the at least one critical dimension comprises forming a statistical combination of the plurality of critical dimensions.

12. The method of claim 1, wherein comparing the at least one characteristic parameter associated with the at least one non-device structure and the at least one characteristic parameter associated with at least one device structure comprises correlating the at least one characteristic parameter associated with the at least one non-device structure and the at least one characteristic parameter associated with the at least one device structure.

13. The method of claim 1, wherein comparing the at least one characteristic parameter associated with the at least one non-device structure and the at least one characteristic parameter associated with at least one device structure comprises comparing a statistical combination of a plurality of characteristic parameters associated with the at least one non-device structure and a statistical combination of a plurality of characteristic parameters associated with the at least one device structure.

14. The method of claim 1, wherein comparing the at least one characteristic parameter associated with the at least one non-device structure and the at least one characteristic parameter associated with the at least one device structure comprises determining at least one bias between the at least one characteristic parameter associated with the at least one non-device structure and the at least one characteristic parameter associated with the at least one device structure.

15. The method of claim 14, wherein determining at least one bias comprises determining at least one of an additive and a multiplicative bias.

16. The method of claim 14, further comprising determining whether the bias is within an allowed range.

17. The method of claim 16, wherein determining whether the bias is within the allowed range comprises determining whether the bias is within the allowed range based upon historical data indicative of one or more historical biases.

18. A method, comprising:
determining at least one characteristic parameter associated with at least one non-device structure on at least one workpiece;
determining at least one characteristic parameter associated with at least one device structure on the at least one workpiece;
comparing the at least one characteristic parameter associated with the at least one non-device structure and the at least one characteristic parameter associated with at least one device structure, wherein comparing the at least one characteristic parameter associated with the at least one non-device structure and the at least one characteristic parameter associated with the at least one device structure comprises determining at least one bias between the at least one characteristic parameter associated with the at least one non-device structure and the at least one characteristic parameter associated with the at least one device structure;
determining whether the bias is within an allowed range; and
generating, in response to determining that the bias is not within the allowed range, a signal indicating that the bias is not within the allowed range.

19. The method of claim 18, further comprising modifying processing of workpieces in response to the signal indicating that the bias is not within the allowed range.

20. The method of claim 19, wherein modifying processing of workpieces in response to the signal indicating that the bias is not within the allowed range comprises stopping processing of workpieces in response to the signal indicating that the bias is not within the allowed range.

21. The method of claim 20, wherein modifying processing of workpieces in response to the signal indicating that the bias is not within the allowed range comprises resuming processing of additional workpieces substantially after stopping processing in response to the signal indicating that the bias is not within the allowed range.

22. The method of claim 19, wherein modifying processing of workpieces in response to the signal indicating that the bias is not within the allowed range comprises taking a corrective action in response to the signal indicating that the bias is not within the allowed range.

23. The method of claim 16, further comprising processing at least one additional workpiece in response to determining that the bias is within an allowed range.

* * * * *